(12) United States Patent
Kiguchi et al.

(10) Patent No.: US 8,895,620 B2
(45) Date of Patent: *Nov. 25, 2014

(54) PEST CONTROLLING COMPOSITION AND METHOD FOR CONTROLLING PEST

(75) Inventors: So Kiguchi, Takarazuka (JP); Soichi Tanaka, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/824,051

(22) PCT Filed: Oct. 13, 2011

(86) PCT No.: PCT/JP2011/074093
§ 371 (c)(1),
(2), (4) Date: Mar. 18, 2013

(87) PCT Pub. No.: WO2012/050235
PCT Pub. Date: Apr. 19, 2012

(65) Prior Publication Data
US 2013/0190329 A1     Jul. 25, 2013

(30) Foreign Application Priority Data
Oct. 14, 2010    (JP) .................. 2010-231367

(51) Int. Cl.
| | | |
|---|---|---|
| *A01N 37/18* | (2006.01) | |
| *A61K 31/16* | (2006.01) | |
| *A01N 43/40* | (2006.01) | |
| *A61K 31/44* | (2006.01) | |
| *A01N 43/46* | (2006.01) | |
| *A61K 31/315* | (2006.01) | |
| *A01N 37/36* | (2006.01) | |
| *A01N 43/60* | (2006.01) | |
| *A01N 43/56* | (2006.01) | |

(52) U.S. Cl.
CPC .............. *A01N 43/60* (2013.01); *A01N 37/36* (2013.01); *A01N 37/18* (2013.01); *A01N 43/56* (2013.01)
USPC ............ 514/613; 514/341; 514/407; 424/405

(58) Field of Classification Search
USPC ..................... 514/613, 341, 407; 424/405
See application file for complete search history.

(56) References Cited

U.S. PATENT DOCUMENTS 5,948,819 A    9/1999 Ohtsuka et al.

FOREIGN PATENT DOCUMENTS

| CA | 2 324 460 A1 | 9/1999 |
| WO | WO 95/27693 A1 | 10/1995 |
| WO | WO 99/48366 A1 | 9/1999 |
| WO | WO 02/10101 A1 | 2/2002 |
| WO | WO 2008/095913 A2 | 8/2008 |
| WO | WO 2009/119872 | * 10/2009 |
| WO | WO 2010/092119 A1 | 8/2010 |

OTHER PUBLICATIONS

International Preliminary Report on Patentability, issued Apr. 16, 2013, for International Application No. PCT/JP2011/074093.
International Search Report, mailed Jul. 23, 2012, for International Application No. PCT/JP2011/074093.
Notification Concerning Transmittal of International Preliminary Report on Patentability, mailed Apr. 25, 2013, for International Application No. PCT/JP2011/074903.
Written Opinion of the International Searching Authority, mailed Jul. 23, 2012, for International Application No. PCT/JP2011/074093.
Ichiba et al., "Fungicidal Activities of α-Methoxyphenylacetic Acid Derivatives", Journal of Pesticide Science, vol. 27, No. 2, 2002, pp. 118-126.
Shibuya Index (Index of Pesticides)—13th Edition, 2008, Shibuya Index Research Group, (7 pages).
Tomlin, The Pesticide Manual: A World Compendium—Fifteenth Edition, 2009, British Corp Production Council, (6 pages).

* cited by examiner

*Primary Examiner* — Uma Ramachandran
(74) *Attorney, Agent, or Firm* — Birch, Stewart, Kolasch & Birch, LLP

(57) ABSTRACT

The present invention provides a composition having an excellent controlling activity on a pest. The composition comprising a compound represented by Formula (1) and one or more 1-(2,6-dichloro-α,α,α-trifluoroparatolyl)pyrazole compound(s) selected from Group (A) shows an excellent controlling activity on a pest. Group (A): a group consisting of acetoprole, ethiprole, fipronil, vaniliprole, pyriprole and pyrafluprole.

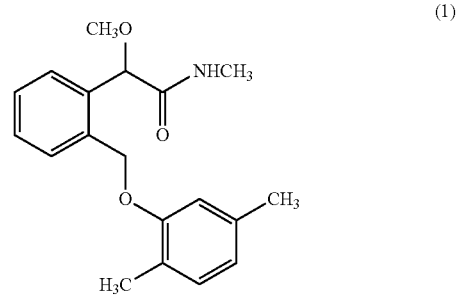

(1)

3 Claims, No Drawings

PEST CONTROLLING COMPOSITION AND METHOD FOR CONTROLLING PEST

TECHNICAL FIELD

The present invention relates to a pest controlling composition and a method for controlling a pest.

BACKGROUND ART

Hitherto, there has been provided compounds as an active ingredient for a composition for controlling a pest (see e.g., The Pesticide Manual—15th edition (BCPC published) ISBN 1901396188; and SHIBUYA INDEX (Index of Pesticides) 13th Edition 2008 (SHIBUYA INDEX RESEARCH GROUP published) ISBN 9784881371435).

Also there has been provided a compound of Formula (1):

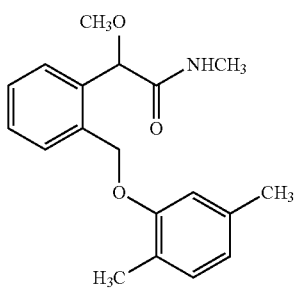

(1)

(see e.g., WO 95/27693 pamphlet and WO 02/10101 pamphlet).

DISCLOSURE OF INVENTION

An object of the present invention is to provide a composition having an excellent control effect on a pest.

The present inventors have intensively studied to find out a composition having an excellent control effect on a pest. As a result, they have found that a composition comprising the compound represented by Formula (1) and one or more 1-(2,6-dichloro-α,α,α-trifluoroparatolyl)pyrazole compound(s) selected from the following group (A) shows a synergistic activity, and thus has an excellent control effect on a pest, and therefore the present invention has been completed.

The present invention provides:

[1] A pest controlling composition comprising a compound represented by Formula (1):

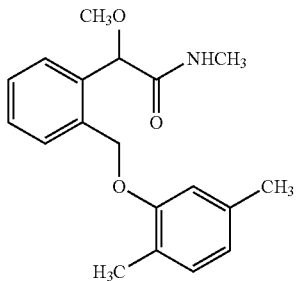

(1)

and one or more 1-(2,6-dichloro-α,α,α-trifluoroparatolyl)pyrazole compound(s) selected from Group (A):

Group (A): a group consisting of acetoprole, ethiprole, fipronil, vaniliprole, pyriprole and pyrafluprole.

[2] The pest controlling composition according to the above [1], wherein the weight ratio of the compound represented by Formula (1) to the 1-(2,6-dichloro-α,α,α-trifluoroparatolyl)pyrazole compound(s) is from 0.0125/1 to 500/1.

[3] The pest controlling composition according to the above [1] or [2], wherein the compound represented by Formula (1) has R-absolute configuration.

[4] A method for controlling a pest, wherein the method comprises applying an effective amount in total of a compound of Formula (1):

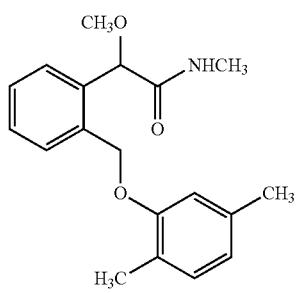

(1)

and one or more 1-(2,6-dichloro-α,α,α-trifluoroparatolyl) pyrazole compound(s) selected from Group (A) to a plant or a soil for cultivating the plant, Group (A): a group consisting of acetoprole, ethiprole, fipronil, vaniliprole, pyriprole and pyrafluprole.

[5] The method according to the above [4], wherein the compound of Formula (1) and the 1-(2,6-dichloro-α,α,α-trifluoroparatolyl)pyrazole compound(s) are applied to a seed.

[6] The method according to the above [4] or [5], wherein the weight ratio of the compound represented by Formula (1) to the 1-(2,6-dichloro-α,α,α-trifluoroparatolyl)pyrazole compound(s) is from 0.0125/1 to 500/1.

[7] The method according to any one of the above [4] to [6], wherein the compound represented by Formula (1) has R-absolute configuration.

[8] Use of a combination of a compound represented by Formula (1):

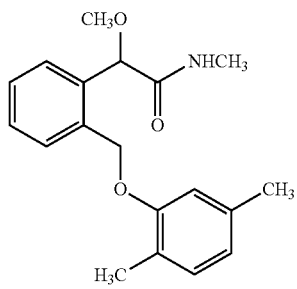

(1)

and one or more 1-(2,6-dichloro-α,α,α-trifluoroparatolyl) pyrazole compound(s) selected from Group (A) for controlling a pest, Group (A): a group consisting of acetoprole, ethiprole, fipronil, vaniliprole, pyriprole and pyrafluprole.

The present invention enables to control a pest.

MODE FOR CARRYING OUT THE INVENTION

A pest controlling composition of the present invention (hereinafter, referred to as a composition of the present invention) comprises a compound represented by Formula (1):

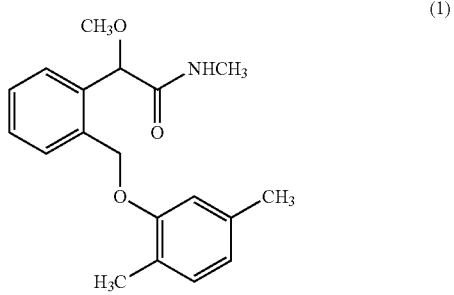

(hereinafter, referred to as an amide compound of the present invention) and one or more 1-(2,6-dichloro-α,α,α-trifluoroparatolyl)pyrazole compound(s) selected from Group (A) (hereinafter, referred to as a pyrazole compound of the present invention), Group (A): a group consisting of acetoprole, ethiprole, fipronil, vaniliprole, pyriprole and pyrafluprole.

The present amide compound is described in for example, WO 95/27693 pamphlet and WO 02/10101 pamphlet, and thus can be prepared according to the method described therein.

The present amide compound has one asymmetric carbon. Herein, a compound represented by Formula (1) wherein an enantiomer having R-absolute configuration is enriched is referred to as an amide compound having R-absolute configuration.

The present amide compound encompasses the following compounds:

compounds represented by Formula (1) wherein an enantiomer having R-absolute configuration amounts to 70% and more of the total amount thereof;

compounds represented by Formula (1) wherein an enantiomer having R-absolute configuration amounts to 90% and more of the total amount thereof;

compounds represented by Formula (1) wherein an enantiomer having R-absolute configuration in 95% and more of the total amount thereof.

Ethiprole and fipronil to be used in the present invention are known compounds having 1-(2, 6-dichloro-α,α,α-trifluoroparatolyl)pyrazole structure, which are described in for example, "The PESTICIDE MANUAL—15th EDITION (BCPC published) ISBN 1901396188", pages 443 and 500 respectively. These compounds are either commercially available, or can be prepared by a known method.

Acetoprole, vaniliprole, pyriprole and pyrafluprole to be used in the present invention are known compounds having 1-(2,6-dichloro-α,α,α-trifluoroparatolyl)pyrazole structure, which are described in for example, "SHIBUYA INDEX (Index of Pesticides) 13th Edition 2008 (SHIBUYA INDEX RESEARCH GROUP published) ISBN 9784881371435", page 59. These compounds are either commercially available, or can be prepared by a known method.

The weight ratio of the present amide compound to the present pyrazole compound(s) in the composition of the present invention is usually from 0.0125/1 to 500/1 (the present amide compound/the present pyrazole compound(s)), preferably 0.025/1 to 100/1, and more preferably 0.1/1 to 10/1.

Although the composition of the present invention may be a mixture as itself of the present amide compound and the present pyrazole compound(s), the composition of the present invention is usually prepared by mixing the present amide compound, the present pyrazole compound(s) and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on. Such formulations can be used by itself or with an addition of other inert components as an agent for controlling a pest.

Usually, the composition of the present invention can contain 0.1 to 99% by weight, preferably 0.2 to 90% by weight, and more preferably 1 to 80% by weight of the present amide compound and the present pyrazole compound(s) in total.

Examples of a solid carrier used on the formulation include finely-divided powder or particles of clay consisting of minerals (e.g., kaolin clay, attapulgite clay, bentonite, montmorillonite, acid clay, pyrophyllite, talc, diatomaceous earth, or calcite), natural organic substances (e.g., corncob powder, or walnut shell powder), synthetic organic substances (e.g., urea), salts (e.g., calcium carbonate, or ammonium sulfate), synthetic inorganic substances (e.g., synthetic hydrous silicon oxide) and so on. Examples of a liquid carrier include aromatic hydrocarbons (e.g., xylene, alkyl benzene, or methylnaphtalene), alcohols (e.g., 2-propanol, ethylene glycol, propylene glycol, or ethylene glycol monoethyl ether), ketones (e.g., acetone, cyclohexanone, or isophorone), vegetable oils (e.g., soybean oil, or cotton oils), petroleum-derived aliphatic hydrocarbons, esters, dimethylsulfoxide, acetonitrile and water.

Examples of the surfactant include anionic surfactant (e.g., alkyl sulfate salts, alkylaryl sulfate salts, dialkyl sulfosuccinate salts, polyoxyethylene alkylaryl ether phosphates, lignin sulfonate, or naphthalenesulfonate formaldehyde polycondensation), nonionic surfactant (e.g., polyoxyethylene alkylaryl ether, polyoxyethylene alkyl polyoxypropylene block copolymer, or sorbitan fatty acid ester) and cationic surfactant (e.g., alkyltrimethyl ammonium salts).

Examples of the other pharmaceutical additives include water-soluble polymer (e.g., polyvinyl alcohol, or polyvinyl pyrrolidone), polysaccharides (e.g. arabic gum, alginic acid and salts thereof, CMC (carboxymethyl-cellulose), or xanthan gum), inorganic substances (e.g, aluminum magnesium silicate, or alumina-sol), antiseptic agent, coloring agent, and PAP (isopropyl acid phosphate), and stabilizing agent (e.g., BHT).

The composition of the present invention can also be prepared by separately formulating the present amide compound and the present pyrazole compound(s) into different formulations by the above procedures, if necessary, further diluting each of them with water, thereafter, mixing the separately prepared different formulations or the dilute solutions.

The composition of the present invention may further contain one or more other fungicide(s) and/or insecticide(s).

The composition of the present invention is used to control a pest by applying it to a plant or a soil for cultivating the plant.

The arthropod pests on which the composition of the present invention exhibits a controlling effect are exemplified below:

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lyes lineolaris*); whiteflies (Aleyrodidae) such as greenhouse whitefly (*Trialeurodes vaporariorum*), sweetpotato whitefly (*Bemisia tabaci*), and silverleaf whitefly (*Bemisia argentifolii*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*); lace bugs (Tingidae); psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Micractis nubilalis* (*Ostrinia furnacalis*), European corn borer (*Ostrinia nubilaris*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plasia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoniella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*), etc.;

Diptera:

Leafminer flies (Agromyzidae) such as onion maggot (*Hylemya antiqua*), seed corn maggot (*Hylemya platura*), rice leafminer (*Agromyza oryzae*), rice leafminer (*Hydrellia griseola*), rice stem maggot (*Chlorops oryzae*), legume leafminer (*Liriomyza trifolii*); melon fly (*Dacus cucurbitae*), and Mediterranean fruit fly (*Ceratitis capitata*), etc.;

Coleoptera:

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), Corn root worms (*Diabrotica* spp.) Colorado beetle (*Leptinotarsa decemlineata*), click beetles (*Agriotes* spp.), and cigarette beetle (*Lasioderma serricorne*), etc.;

Orthoptera:

African mole cricket (*Gryllotalpa africana*), rice grasshopper (*Oxya yezoensis*), and rice grasshopper (*Oxya japonica*), etc.;

Hymenoptera:

Cabbage sawfly (*Athalia rosae*, leaf-cutting ant (*Acromyrmex* spp.), and fire ant (*Solenopsis* spp.), etc.;

Acarina:

Spider mites (Tetranychidae) such as two-spotted spider mite (*Tetranychus urticae*), citrus red mite (*Panonychus citri*), and *Oligonychus* spp.; eriophyid mites (Eriophyidae) such as pink citrus rust mite (*Aculops pelekassi*); tarosonemid mites (Tarsonemidae) such as broad mite (*Polyphagotarsonemus latus*); false spider mites (Tenuipalpidae); tuckerellidae; acarid mites (Acaridae) such as mold mite (*Tyrophagus putrescentiae*); house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei;*

Nematodes:

White tip nematode (*Aphelenchoides besseyi*), and strawberry bud nematode (*Nothotylenchus acris*), etc.

The plant diseases which can be controlled by the present invention are exemplified below:

Rice diseases: blast (*Magnaporthe oryzae*), helminthosporium leaf spot (*Cochliobolus miyabeanus*), sheath blight (*Rhizoctonia solani*) and bakanae disease (*Gibberella fujikuroi*);

Diseases of barley, wheat, oats and rye: powdery mildew (*Erysiphe graminis*), Fusarium head blight (*Fusarium graminearum, F. avenaceum, F. culmorum, F. asiaticum, Microdochium nivale*), rust (*Puccinia striiformis, P. graminis, P. recondite, P. hordei*), snow blight (*Typhula sp., Micronectriella nivalis*), loose smut (*Ustilago tritici, U. nuda*), bunt (*Tilletia caries*), eyespot (*Pseudocercosporella herpotrichoides*), scald (*Rhynchosporium secalis*), leaf blotch (*Septoria tritici*), glume blotch (*Leptosphaeria nodorum*) and net blotch (*Pyrenophora teres* Drechsler);

Citrus diseases: melanose (*Diaporthe citri*), scab (*Elsinoe fawcetti*), green mold (*Penicillium digitatum*) and blue mold (*Penicillium italicum*);

Apple diseases: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), bitter rot (*Colletotrichum acutatum*) and late blight (*Phytophtora cactorum*);

Pear diseases: scab (*Venturia nashicola, V. pirina*), black spot (*Alternaria alternata* Japanese pear pathotype), rust (*Gymnosporangium asiaticum*) and late blight (*Phytophtora cactorum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*) and Gray mold (*Botrytis cinerea*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), gray mold fungus (*Botrytis cinerea*) and damping-off (*Pythium* sp.);

Tomato diseases: early blight (*Alternaria solani*), leaf mold (*Cladosporium fulvum*) and late blight (*Phytophthora infestans*);

Egg plant disease: brown spot (*Phomopsis vexans*) and powdery mildew (*Erysiphe cichoracearum*);

Diseases of Cruciferous Vegetables: *Alternaria* leaf spot (*Alternaria japonica*), white spot (*Cercosporella brassicae*), clubroot (*Plasmodiophora brassicae*), and downy mildew (*Peronospora parasitica*);

Rapeseed diseases: *Sclerotinia* rot (*Sclerotinia sclerotiorum*), black spot (*Alternaria brassicae*), powdery mildew (*Erysiphe cichoracearum*), blackleg (*Leptosphaeria maculans*);

Welsh onion diseases: rust (*Puccinia allii*);

Soybean diseases: purple seed stain (*Cercospora kikuchii*), *Sphaceloma* scad (*Elsinoe glycines*), pod and stem blight (*Diaporthe phaseolorum* var. *sojae*), rust (*Phakopsora pachyrhizi*) and *phytophthora* stem rot (*Phytophthora sojae*);

Adzuki-bean diseases: Gray mold (*Botrytis cinerea*), *Sclerotinia* rot (*Sclerotinia sclerotiorum*);

Kidney bean diseases: Gray mold (*Botrytis cinerea*), *Sclerotinia* rot (*Sclerotinia sclero tiorum*), anthracnose (*Colletotrichum lindemthianum*);

Peanut diseases: leaf spot (*Cercospora personata*), brown leaf spot (*Cercospora arachidicola*) and southern blight (*Sclerotium rolfsii*);

Garden pea diseases: powdery mildew (*Erysiphe pisi*);

Potato diseases: early blight (*Alternaria solani*) and late blight (*Phytophthora infestans*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Cotton diseases: *fusarium* wilt (*Fusarium oxysporum*), damping-off (*Rhizoctonia solani*);

Tabacco diseases: brown spot (*Alternaria longipes*), powdery mildew (*Erysiphe cichoracearum*), anthracnose (*Colletotrichum tabacum*), downy mildew (*Peronospora tabacina*) and late blight (*Phytophthora nicotianae*);

Sugar beet diseases: *Cercospora* leaf spot (*Cercospora beticola*), leaf blight (*Thanatephorus cucumeris*), Root rot (*Thanatephorus cucumeris*), *Aphanomyces* root rot (*Aphanidermatum cochlioides*);

Rose diseases: black spot (*Diplocarpon rosae*) and powdery mildew (*Sphaerotheca pannosa*);

*Chrysanthemum* diseases: leaf blight (*Septoria chrysanthemi-indici*) and white rust (*Puccinia horiana*);

Various plants diseases: diseases caused by *Pythium* spp. (*Pythium aphanidermatum, Pythium debarianum, Pythium graminicola, Pythium irregulare, Pythium ultimum*), Gray mold (*Botrytis cinerea*), Sclerotinia rot (*Sclerotinia sclerotiorum*), Japanese radish diseases: *Alternaria* leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola, Pseudocercospora musae*).

Examples of the plants to which the composition of the present invention can be applied are as follows:

Crops: corn, rice, wheat, barley, rye, oat, *sorghum*, cotton, soybean, adzuki-bean, kidney bean, peanut, buckwheat, beet, rapeseed, sunflower, sugar cane, and tobacco, etc.;

Vegetables: solanaceous vegetables (eggplant, tomato, pimento, pepper, and potato, etc.), cucurbitaceous vegetables (cucumber, pumpkin, zucchini, water melon, melon, and squash, etc.), cruciferous vegetables (Japanese radish, white turnip, horseradish, kohlrabi, Chinese cabbage, cabbage, leaf mustard, broccoli, and cauliflower, etc.), asteraceous vegetables (burdock, crown daisy, artichoke, and lettuce, etc.), liliaceous vegetables (green onion, onion, garlic, and asparagus), ammiaceous vegetables (carrot, parsley, celery, and parsnip, etc.), chenopodiaceous vegetables (spinach, and Swiss chard, etc.), lamiaceous vegetables (*Perilla frutescens*, mint, and basil, etc.), strawberry, sweet potato, Japanese yam, and taro, etc.;

Flowers;

Foliage plants;

Turfgrass;

Fruits: pomaceous fruits (apple, pear, Japanese pear, Chinese quince, and quince, etc.), stone fleshy fruits (peach, plum, nectarine, Japanese apricot, cherry fruit, apricot, and prune, etc.), *citrus* fruits (*Citrus unshiu*, orange, lemon, lime, and grapefruit, etc.), nuts (chestnut, walnuts, hazelnuts, almond, pistachio, cashew nuts, and macadamia nuts, etc.), berrys (blueberry, cranberry, blackberry, and raspberry, etc.), grape, kaki persimmon, olive, Japanese plum, banana, coffee, date palm, and coconuts, etc.; and Trees other than fruit trees: tea, mulberry, flowering plant, roadside trees (ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*), etc.

The aforementioned "plants" include plants which resistances have been imparted by genetic recombination.

Exemplary embodiments of the composition of the present invention are as follows:

a composition comprising the present amide compound and acetoprole wherein the weight ratio of the present amide compound to acetoprole is from 0.0125/1 to 500/1;

a composition comprising the present amide compound and acetoprole wherein the weight ratio of the present amide compound to acetoprole is from 0.025/1 to 100/1;

a composition comprising the present amide compound and acetoprole wherein the weight ratio of the present amide compound to acetoprole is from 0.1/1 to 10/1;

a composition comprising the present amide compound and ethiprole wherein the weight ratio of the present amide compound to ethiprole is from 0.0125/1 to 500/1;

a composition comprising the present amide compound and ethiprole wherein the weight ratio of the present amide compound to ethiprole is from 0.025/1 to 100/1;

a composition comprising the present amide compound and ethiprole wherein the weight ratio of the present amide compound to ethiprole is from 0.1/1 to 10/1;

a composition comprising the present amide compound and fipronil wherein the weight ratio of the present amide compound to fipronil is from 0.0125/1 to 500/1;

a composition comprising the present amide compound and fipronil wherein the weight ratio of the present amide compound to fipronil is from 0.025/1 to 100/1;

a composition comprising the present amide compound and fipronil wherein the weight ratio of the present amide compound to fipronil is from 0.1/1 to 10/1;

a composition comprising the present amide compound and vaniliprole wherein the weight ratio of the present amide compound to vaniliprole is from 0.0125/1 to 500/1;

a composition comprising the present amide compound and vaniliprole wherein the weight, ratio of the present amide compound to vaniliprole is from 0.025/1 to 100/1;

a composition comprising the present amide compound and vaniliprole wherein the weight ratio of the present amide compound to vaniliprole is from 0.1/1 to 10/1;

a composition comprising the present amide compound and pyriprole wherein the weight ratio of the present amide compound to pyriprole is from 0.0125/1 to 500/1;

a composition comprising the present amide compound and pyriprole wherein the weight ratio of the present amide compound to pyriprole is from 0.025/1 to 100/1;

a composition comprising the present amide compound and pyriprole wherein the weight ratio of the present amide compound to pyriprole is from 0.1/1 to 10/1;

a composition comprising the present amide compound and pyrafluprole wherein the weight ratio of the present amide compound to pyrafluprole is from 0.0125/1 to 500/1;

a composition comprising the present amide compound and pyrafluprole wherein the weight ratio of the present amide compound to pyrafluprole is from 0.025/1 to 100/1; and a composition comprising the present amide compound and pyrafluprole wherein the weight ratio of the present amide compound to pyrafluprole is from 0.1/1 to 10/1.

The method for controlling a pest of the present invention (hereinafter, referred to as the method for controlling of the present invention) comprises applying an effective amount in total of the present amide compound and the present pyrazole compound(s) to the plants or the soil for cultivating the plant. Such plants include foliages of plant, seeds of plant, or bulbs of plant. The bulbs herein are intended to mean bulb, corm, rootstock, tuber, tuberous root and rhizophore.

In the method for controlling of the present invention, the present amide compound and the present pyrazole compound(s) may be applied separately around the same time to the plant or the soil for cultivating the plant, but is usually applied as the composition of the present invention because of a convenience on applying.

In the method for controlling of the present invention, examples of the method of applying the present amide compound and the present pyrazole compound(s) include foliage treatment, soil treatment, root treatment and seed treatment.

Such foliage treatment includes a method of applying the composition of the present invention to a surface of the plant to be cultivated by a foliage application or a stem application.

Such root treatment includes a method of soaking a whole or a root of the plant into a medicinal solution comprising the present amide compound and the present pyrazole compound(s), and a method of attaching a solid formulation comprising the present amide compound, the present pyrazole compound(s) and the solid carrier to a root of the plant.

Such soil treatment includes soil broadcast, soil incorporation, and irrigation of the medicinal solution to a soil.

Such seed treatment includes an applying of the composition of the present invention to a seed or a bulb of the plant to be prevented from the plant disease, specifically, a spray treatment by spraying a suspension of the composition of the present invention in a mist form to a surface of a seed or a surface of a bulb, a smear treatment by smearing the wettable powder, the emulsifiable concentrate or the flowable formulation of the composition of the present invention with an addition of small amounts of water or as itself to a seed or a bulb, an immerse treatment of a seed into a solution of the composition of the present invention for a given time, a film-coating treatment, and a pellet-coating treatment.

Each dose, of the present amide compound and the present pyrazole compound(s) in the method for controlling of the present invention may vary depending on a kind of plant to be treated, a kind or a frequency of an occurrence of a plant disease as a control subject, a dosage form, a treatment period, a treatment method, a treatment site, a climate condition, etc. In case of an application to a foliage of the plant or a soil for cultivating the plant, a total amount of the present amide compound and the present pyrazole compound(s) is usually 1 to 500 g, preferably 2 to 200 g, and more preferably 10 to 100 g, per 1000 $m^2$. Each dose of the present amide compound and the present pyrazole compound(s) in the treatment for seed is usually 0.001 to 10 g, and preferably 0.01 to 1 g, per 1 kg of seeds as a total amount of the present amide compound and the present pyrazole compound(s).

The emulsifiable concentrate, the wettable powder or the flowable formulation, etc., is usually applied by diluting them with water, and then spreading them. In this case, usually, each concentration of the present amide compound and the present pyrazole compound(s) contains 0.0005 to 2% by weight, and preferably 0.005 to 1% by weight of the present amide compound and the present pyrazole compound(s) in total. The dust formulation or the granular formulation, etc, is usually applied as itself without diluting them.

EXAMPLES

Next, the present invention is described in more detail below by the following examples including formulation examples and test examples, but the present invention should not be construed to be limited thereto.

The formulation examples are given below. It is to be noted that in the formulation examples, the term "part" indicates "part by weight".

Formulation 1

5 parts of the present amide compound, 5 parts of acetoprole, 35 parts of the mixture of white carbon and polyoxyethylene alkylether sulfate anmmonium salts (weight ratio 1:1), and 55 parts of water are mixed and the resulting solution is then subjected to fine grinding according to wet grinding method, so as to obtain a flowable formulation. The same above operations are carried out using ethiprole, fipronil, vaniliprole, pyriprole or pyrafluprole instead of acetoprole, so as to obtain flowable formulations.

Formulation 2

10 parts of the present amide compound, 5 parts of acetoprole and 1.5 parts of sorbitan trioleate are mixed into 28 parts of an aqueous solution that contains 2 parts of polyvinyl alcohol, and the mixed solution is then subjected to fine grinding according to wet grinding method. Thereafter, 45.50 parts of an aqueous solution that contains 0.05 parts of xanthan gum and 0.1 part of aluminum magnesium silicate is added to the resultant, and 10 parts of propylene glycol is further added thereto. The obtained mixture is blended by stirring, so as to obtain the flowable formulation. The same above operations are carried out using ethiprole, fipronil, vaniliprole, pyriprole or pyrafluprole instead of acetoprole, so as to obtain flowable formulations.

Formulation 3

10 parts of the present amide compound, 40 parts of acetoprole, 3 parts of calcium lignosulfonate, 2 parts of sodium lauryl sulfate, and 45 parts of synthetic hydrous silicon oxide are fully crushed and mixed, so as to obtain wettable powders. The same above operations are carried out using ethiprole, fipronil, vaniliprole, pyriprole or pyrafluprole instead of acetoprole, so as to obtain wettable powders.

The test examples are given below.

Test Examples 1 to 2

True leaf of cucumber was punched out with cork borer to 13 mm in diameter to prepare a leaf disk. In 24 well microwell plate that was dispensed with 1 ml 0.8% water agar, the leaf disk was placed such that the upper side of the leaf was in an upward direction. Thereto was spread 20 micro liter a testing solution prepared by mixing the present amide compound and fipronil to a predetermined concentration (for treated group). Control where 20 micro liter ion-exchange water was spread was prepared (for non-treated group). After confirming that the spray solution was dried, conidium of gray mold fungus (Botrytis cinerea) was suspended into potato dextrose broth (DIFCO) in density of about $10^5$ conidia/mL and was then subjected to a spray inoculation. After leaving to stand the leaf disk in a growth chamber set up at 15° C. for six days, an onset area on each leaf was measured and a preventive value was then calculated by the following equation 1.

Preventive value (%)=100×(A−B)/A  (Equation 1)

wherein

A: an onset area rate of plant belonging to non-treated group

B: an onset area rate of plant belonging to treated group onset area rate=(onset area of the leaf disk)/(the total area of the leaf disk)

The results are shown in Table 1.

TABLE 1

| Ex. No. | treatment concentration (ppm) | | preventive value (%) |
|---|---|---|---|
| | the present amide compound | fipronil | |
| 1 | 2.5 | 0.5 | 100 |
| 2 | 1.0 | 5.0 | 100 |

Test Examples 3 to 4 and Comparative Examples 1 to 2

The same above operations as described in Test Examples 1 to 2 were carried out using ethiprole instead of fipronil, so as to obtain the respective preventive values.

Also the same operations as described in Test Examples 1 to 2 were carried out except that the testing medicine solution was substituted with a predetermined concentration of a dimethyl sulfoxide solution of the present amide compound, so as to calculate the respective preventive values.

The results are shown in Table 2.

TABLE 2

| | treatment concentration (ppm) | | preventive value (%) |
|---|---|---|---|
| | the present amide compound | ethiprole | |
| Ex. No. 3 | 2.5 | 0.5 | 100 |
| Ex. No. 4 | 1.0 | 5.0 | 100 |
| Comp. Ex. No. 1 | 2.5 | — | 56 |
| Comp. Ex. No. 2 | 1.0 | — | 46 |

The invention claimed is:

1. A pest controlling composition comprising a compound of the Formula (1):

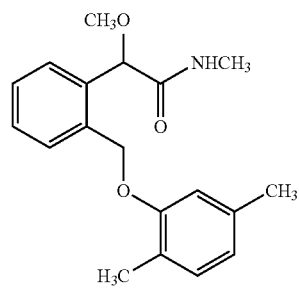

and one or more 1-(2,6-dichloro-α,α,α-trifluoroparatolyl) pyrazole compound(s) selected from Group (A):

Group (A): a group consisting of ethiprole and fipronil, wherein a weight ratio of the compound of the formula (1) to the 1-(2,6-dichloro-α,α,α-trifluoro-paratolyl)pyrazole compound(s) is from 0.1/1 to 10/1.

2. A method for controlling a pest, wherein the method comprises applying an effective amount in total of a compound of the formula (1):

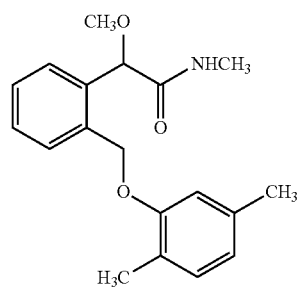

and one or more 1-(2,6-dichloro-α,α,α-trifluoroparatolyl) pyrazole compound(s) selected from Group (A) to a plant or a soil for cultivating the plant, Group (A): a group consisting of ethiprole and fipronil, wherein a weight ratio of the compound of the formula (1) to the 1-(2,6-dichloro-α,α,α-trifluoro-paratolyl)pyrazole compound(s) is from 0.1/1 to 10/1.

3. The method according to claim 2, wherein the compound of Formula (1) and the 1-(2,6-dichloro-α,α,α-trifluoroparatolyl)pyrazole compound(s) are applied to a seed.

* * * * *